United States Patent
Otto

(10) Patent No.: US 9,717,598 B2
(45) Date of Patent: Aug. 1, 2017

(54) PROSTHETIC DEVICE FOR KNEE JOINT AND METHODS OF IMPLANTING AND REMOVING SAME

(75) Inventor: Jason Karl Otto, Plantation, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 1603 days.

(21) Appl. No.: 12/571,960

(22) Filed: Oct. 1, 2009

(65) Prior Publication Data

US 2010/0094429 A1    Apr. 15, 2010

Related U.S. Application Data

(60) Provisional application No. 61/194,954, filed on Oct. 2, 2008.

(51) Int. Cl.
*A61F 2/38* (2006.01)
*A61F 2/30* (2006.01)
*A61F 2/46* (2006.01)

(52) U.S. Cl.
CPC .......... *A61F 2/3877* (2013.01); *A61F 2/389* (2013.01); *A61F 2/3859* (2013.01);
(Continued)

(58) Field of Classification Search
CPC .......... A61F 2/3859; A61F 2002/3895; A61F 2002/3863; A61F 2002/4631; A61F 2002/30878; A61F 2002/30879; A61F 2002/30884; A61F 2002/30883; A61B 17/1764; A61B 17/155; A61B 17/154;
(Continued)

(56) References Cited

U.S. PATENT DOCUMENTS 5,171,276 A * 12/1992 Caspari et al. ............ 623/16.11
6,102,954 A *  8/2000 Albrektsson ....... A61B 17/8605
                                                   623/20.32
(Continued)

FOREIGN PATENT DOCUMENTS

EP    1 872 746 A2    1/2008
JP    H05-503644      6/1993
(Continued)

OTHER PUBLICATIONS

International Search Report dated Dec. 30, 2009 in correspondence with PCT Application No. PCT/US2009/059236.

*Primary Examiner* — Brian Dukert
(74) *Attorney, Agent, or Firm* — Foley & Lardner LLP

(57) ABSTRACT

A prosthetic device for a knee joint includes a body portion and a first keel. The body portion attaches to a bone of a knee joint. The body portion can have a bearing surface configured to replace at least a portion of the bone and an implantation surface configured to face the bone upon implantation. The first keel can be configured to be inserted into a corresponding first keel void formed in the bone. The first feel can be configured to project outwardly from the implantation surface by an amount sufficient to inhibit movement of the body portion relative to the bone in both medial and lateral directions upon insertion into the first keel void. The first keel can extend along a longitudinal direction of the body portion and is offset from a longitudinal centerline of the body portion. Methods of implanting and removing the prosthetic device are also provided.

3 Claims, 14 Drawing Sheets

(52) U.S. Cl.
CPC ............... *A61F 2002/30879* (2013.01); *A61F 2002/30881* (2013.01); *A61F 2002/30884* (2013.01); *A61F 2002/30892* (2013.01); *A61F 2002/3895* (2013.01); *A61F 2002/4619* (2013.01)

(58) Field of Classification Search
CPC ............ A61B 17/1615; A61B 17/1642; A61B 17/1675
USPC .................................. 623/20.19, 20.3, 20.31
See application file for complete search history.

(56) References Cited

U.S. PATENT DOCUMENTS

| | | | | |
|---|---|---|---|---|
| 6,554,838 | B2 * | 4/2003 | McGovern | A61B 17/1764 606/87 |
| 6,554,866 | B1 * | 4/2003 | Aicher et al. | 623/20.29 |
| 2004/0006394 | A1 * | 1/2004 | Lipman et al. | 623/20.29 |
| 2005/0192588 | A1 * | 9/2005 | Garcia | A61B 17/155 606/88 |
| 2007/0100462 | A1 | 5/2007 | Lang et al. | |

FOREIGN PATENT DOCUMENTS

| | | |
|---|---|---|
| JP | 2001-087292 | 4/2001 |
| JP | 2005-532089 | 10/2005 |
| SU | 757159 | 8/1980 |
| WO | WO 2006/004885 A2 | 1/2006 |
| WO | WO 2008/098061 A2 | 8/2008 |

* cited by examiner

PROSTHETIC DEVICE FOR KNEE JOINT AND METHODS OF IMPLANTING AND REMOVING SAME

CROSS-REFERENCE TO RELATED PATENT APPLICATIONS

This application claims priority to U.S. Provisional Patent Application Ser. No. 61/194,954, filed on Oct. 2, 2008, which is hereby incorporated by reference in its entirety.

BACKGROUND OF THE INVENTION

Field of Invention

The present invention relates to a prosthetic device for a knee joint, particularly a prosthetic device for a knee joint having a body portion and a keel, and methods of implanting and removing the same.

Description of Related Art

Prosthetic devices for knee joints, e.g., knee implants, typically have structures on the bone interface surface to facilitate attachment of the prosthetic device to the bone of the knee joint. For example, it is common for a prosthetic device to have one or more pegs and a keel extending outwardly from a longitudinal axis or centerline of the bone interface surface. Such a keel typically is large and projects a significant length from the bone interface surface to facilitate connection of the prosthetic device to the bone and to provide sufficient strength and stiffness for the prosthetic device.

The large, central keel of a conventional prosthetic device can create difficulties during implantation. For example, the large keel requires the formation of a deep void in the bone to receive the keel. Forming this deep void can cause bone preparation time to be longer than desired, and require multiple cutting tools. Moreover, the large keel can cause fracture of bone during implantation, such as when the void is not sufficiently wide and/or deep.

The large keel also can create difficulties during revision, e.g., the removal of the prosthetic device from the bone to allow for its replacement with a new prosthetic device. To be able to remove the implanted prosthetic device, a relatively large amount of bone may need to be resected so that the keel may be removed from its deep insertion into the bone. Also, the keel itself may cause removal of a relatively large amount of bone when the prosthetic device is removed from the bone, especially when cement is used to join the keel to the bone.

A conventional prosthetic device may include a rim or lip around most or all of the outer perimeter of the bone interface surface. When the prosthetic device is fit within a void in the bone, the rim can form a pocket that contains the cement to increase cement pressurization and cement interdigitation into the bone to enhance fixation. The rim itself typically does not sufficiently enhance the strength and stiffness of the prosthetic device.

A conventional prosthetic device also may have a bone interface surface that is configured based on resection techniques. For example, bone may be resected by making multiple planar cuts. Accordingly, a conventional bone interface surface can have multiple substantially planar surfaces to fit properly on the bone. The intersection of those substantially planar surfaces can result in thin material cross-sections, concentrating and increasing stresses, which can lead to failure of the prosthetic device. Moreover, because the prosthetic device must be sufficiently thick at the intersection of substantially planar sections to decrease the likelihood of failure, other areas of the prosthetic device may be thicker than necessary, thus requiring more than an optimal amount of bone removal for implantation.

SUMMARY

According to an embodiment, a prosthetic device for a knee joint can include a body portion and a first keel. The body portion can be for attachment to a bone of a knee joint. The body portion can have a bearing surface configured to replace at least a portion of the bone and an implantation surface configured to face the bone upon implantation. The first keel can be configured to be inserted into a corresponding first keel void formed in the bone. The first feel can be configured to and project outwardly from the implantation surface by an amount sufficient to inhibit movement of the body portion relative to the bone in both medial and lateral directions upon insertion into the first keel void. The first keel can extend along a longitudinal direction of the body portion and is offset from a longitudinal centerline of the body portion.

According to another embodiment, a method of implanting a prosthetic device in a knee joint can include the steps of removing a first portion of a bone of a knee joint and removing a second portion of the bone. The step of removing the first portion of the bone can form a body-portion void configured to receive a body portion of a prosthetic device. The body-portion void can extend into the bone a first body-portion depth from an original surface of the bone. The step of removing the second portion of the bone can form a first keel void to receive a first keel projecting from the body portion of the prosthetic device. The first keel void can extend into the bone a first keel depth from the original surface of the bone. The first keel depth can be greater than the first body-portion depth and the first keel void can be configured to receive the first keel extending along a longitudinal direction of the body portion and offset from a longitudinal centerline of the body portion.

According to another embodiment, a method of removing a prosthetic device from a knee joint can include the steps of resecting bone material from a bone in a knee joint in which a prosthetic device is implanted and removing the prosthetic device from the bone. The prosthetic device can include a body portion and a first keel inserted into a first keel void in the bone to a first keel depth. The first keel can be offset from a longitudinal centerline of the body portion.

BRIEF DESCRIPTION OF THE DRAWINGS

The accompanying drawings, which are incorporated and constitute a part of this specification, illustrate embodiments of the invention and together with the description serve to explain aspects of the invention.

FIG. 8b is a perspective view of the implant of FIG. 8a.

FIG. 9b is an end cross-sectional view of the implant of FIG. 9a.

FIG. 12b is an end view of the implant of FIG. 12a.

FIG. 16b is a cross-sectional view showing a step of forming keel voids in the bone of FIG. 16a.

DETAILED DESCRIPTION OF PREFERRED EMBODIMENTS

Figure 1:
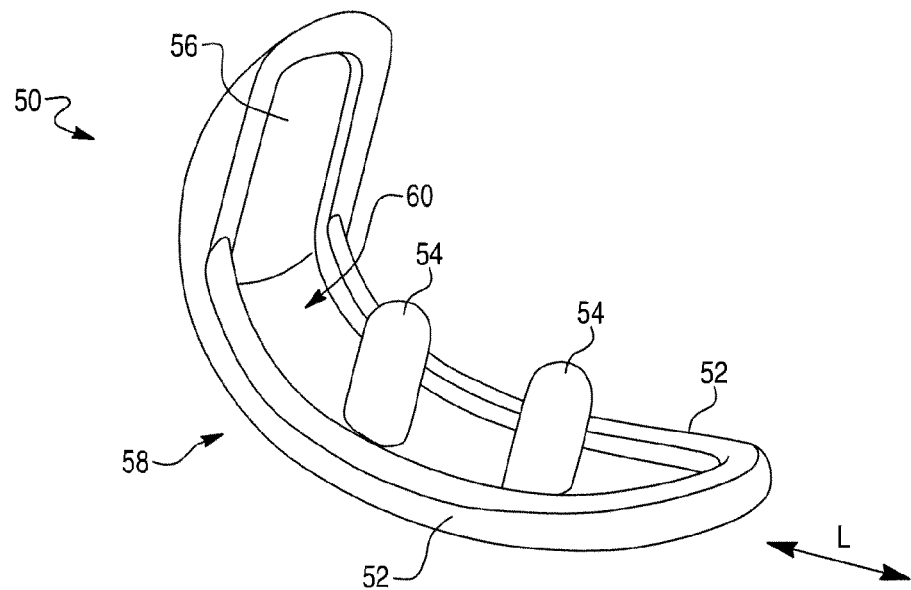
FIG. 1 is a left perspective view of an implant, according to an embodiment.

Presently preferred embodiments of the invention are illustrated in the drawings. An effort has been made to use the same or like reference numbers throughout the drawings to refer to the same or like parts.

Overview

A prosthetic device for a knee joint according to the present invention preferably is a unicompartmental component for replacement of a portion of the knee joint (such as a compartment of the femur), however, it also could be a total knee component. The prosthetic device also could be, for example, a patellofemoral component, a tibial baseplate, or a tibial inlay. The prosthetic device preferably includes a body portion for attachment to a bone of the knee joint and one or more keels.

The body portion of the prosthetic device can be formed from materials that are conventional in the art, or of other materials. The body portion can have a bearing surface that can be configured to replace at least a portion of the bone of the knee joint. The bearing surface preferably is shaped to contact and slide across an opposing implant or bone in the knee joint. The body portion also can have an implantation surface that can be configured to face the bone to which the prosthetic device is attached upon implantation. Preferably at least a portion of the implantation surface contacts that bone. In preferred embodiments, the implantation surface is arcuate and is not a collection of planar surfaces.

The keel of the prosthetic device can be configured to be inserted in a corresponding keel void formed in the bone. The keel projects outwardly from the implantation surface of the body portion by an amount sufficient to inhibit movement of the body portion relative to the bone in both translation (e.g., medial and lateral directions) and axial rotation (e.g., internal and external rotations). According to the present invention, the keel (or at least one of the keels if there is more than one) is offset from a longitudinal centerline of the body portion. The keel or keels can be sufficiently large to facilitate connection of the prosthetic device to the bone and to provide sufficient strength and stiffness for the prosthetic device.

Exemplary Prosthetic Devices

Figure 2:
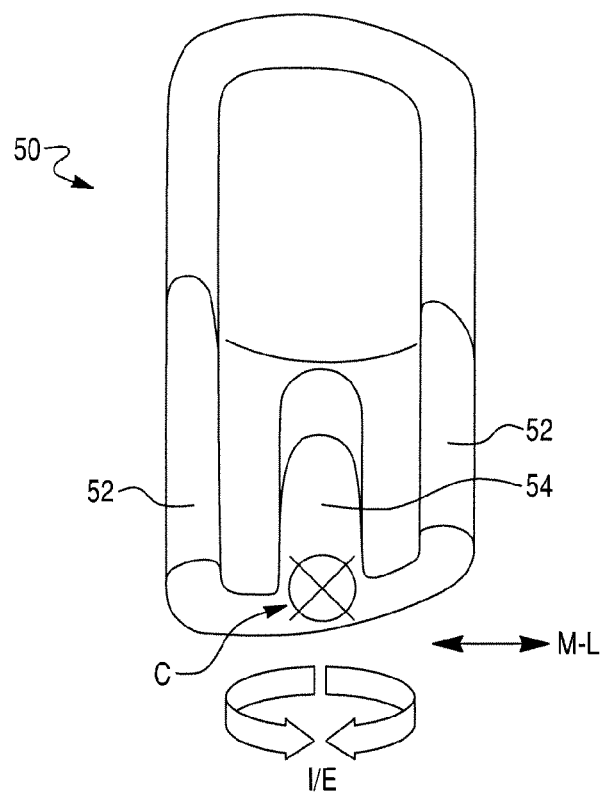
FIG. 2 is a cross sectional end view of the implant of FIG. 1.

FIG. 1 shows a prosthetic device or implant 50, according to an embodiment of the invention. The prosthetic device 50 includes a body portion 56 for attachment to a bone of a joint. The body portion 56 includes a bearing surface 58 and an implantation surface 60. The prosthetic device 50 has a longitudinal direction indicated by arrow L in FIG. 1 and a longitudinal centerline indicated by arrow C entering the page in the example of FIG. 2. FIG. 2 shows an end cross-sectional view of the prosthetic device 50 of FIG. 1 and shows the prosthetic device 50 in relation to the medial-lateral direction of a knee joint, as indicated by arrow M-L.

The prosthetic device 50 can include at least one central peg 54 that is provided in a central region of the implantation surface 60, such as along the longitudinal centerline C of the body portion 56. The central peg 54 is configured be inserted into a void formed in the bone of joint to promote attachment of the prosthetic device 50 to the bone.

The prosthetic device 50, in this embodiment, further includes two keels 52 that can be configured to facilitate connection of the prosthetic device 50 to the bone and to provide sufficient strength and stiffness for the prosthetic device 50. The keels 52 can extend along the longitudinal direction L of the body portion 56. The keels 52 are also both offset from the longitudinal centerline C of the body portion 56.

The keels 52 can have a length protruding from the implantation surface towards the bone that is shorter than the lengths of conventional keels. The keels 52 preferably project a length of no greater than 10 mm from the implantation surface 60. Because two keels 52 are provided, they can be smaller (project less from the implantation surface 60) while providing the same connection, strength, and rigidity as a larger central keel of conventional prosthetic devices. For example, the keels 52 can be configured to project outwardly from the implantation surface 60 by an amount sufficient to inhibit movement of the body portion 56 relative to the bone in both translation (e.g., medial and lateral directions) and axial rotation (e.g., internal and external rotation), as indicated by arrows M-L and I/E in the example of FIG. 2, respectively, upon insertion of the keels 52 into corresponding keel voids in the bone. Though only two keels 52 are shown, additional keels could be provided. Up to a certain limit, the addition of keels allows for a corresponding decrease in the projection length of the keels from the implantation surface 60. In particular, as the number of keels increases, the length that any given keel projects outwardly from the implantation surface can be decreased while maintaining connection, strength, and stiffness. Although larger keels generally provide greater strength and greater attachment for a prosthetic device to a bone due to the greater amount of surface area and penetration into the bone, providing a greater number of keels can offset the loss of surface area caused by providing keels with a shorter projected length due to the overall surface area provided by the plurality of keels. Thus, a prosthetic device may be designed to reduce the amount of bone that would need to be removed to connect the prosthetic device. Reducing the amount of bone removal will also reduce the amount of time needed to cut a void for a device with no keel, but with an overall thickness equivalent to the keel height.

In addition, the keels 52 can have a width in the medial-lateral direction M-L that is greater than the widths of conventional keels. In a preferred embodiment, each of the keels 52 preferably has a width in the medial-lateral direction of 6 mm.

As shown in FIG. 2, each of the surfaces of keels 52 preferably has a convex, arcuate, cross-sectional shape along the medial-lateral direction. Each of the surfaces of the keels 52 also preferably has a concave, arcuate, cross-sectional shape along the longitudinal direction. The surface of the keels can have a shape with an arc radius of, for example, 15-100 mm, or more preferably 30-50 mm.

Because the keels can be configured to have a relatively short length of projection from the from the implantation surface, the keels do not need to penetrate deep into the bone. In addition, the rounded, concave, arcuate shape of the keels can minimize the wedging that may occur with conventional keels, which can lead to fracture of bone, and provides rounded surfaces without stress concentrators, such as sharp, square corners. Thus, the keels of the present invention advantageously minimize fracturing of bone during implantation and minimize the amount of bone removed when a prosthetic device is revised, due to the relatively shallow depth that the keels penetrate into bone.

The keels 52 may extend along or near the perimeter or edge of the implantation surface 60. In the embodiment shown in FIGS. 1 and 2, the keels 52 extend along the perimeter. However, they could be disposed inward of the perimeter at a distance that is preferably no greater than 10 mm.

Figure 3:
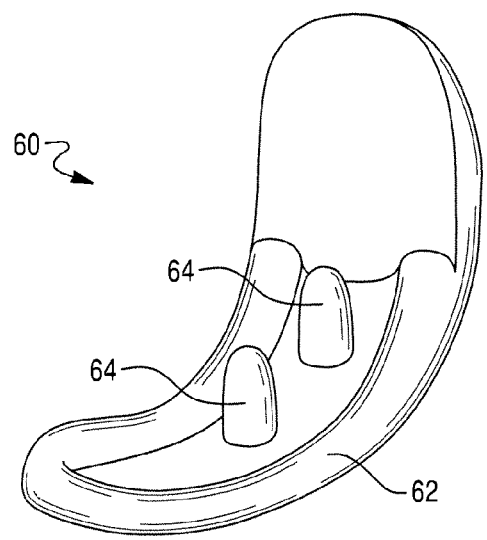
FIG. 3 is a right perspective view of an implant, according to another example.

Though the keels 52 are shown as being a substantially a continuous structure around the perimeter in FIGS. 1 and 2, they are considered to be two keels because they create two projections from the implantation surface 60 in the medial-lateral cross-section of FIG. 2. Alternatively, keels 62 can be configured to be continuous around only a portion of the perimeter, as shown by the example in FIG. 3 of another prosthetic device 60 (central pegs 64 are also provided in this embodiment). As a further alternative, the keels 52, 62 can be entirely distinct from one another (not shown).

Figure 4:
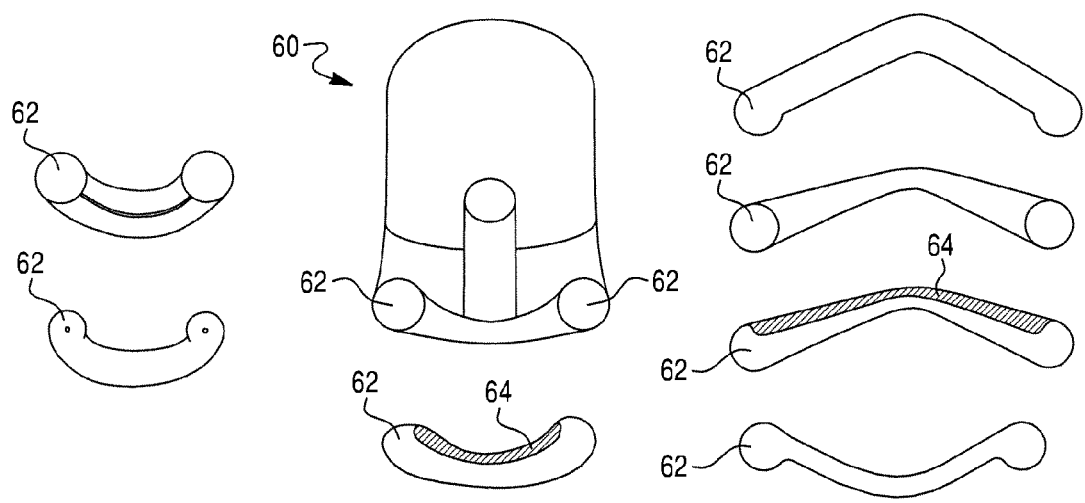
FIG. 4 shows end views of various exemplary implants.

Prosthetic devices according to the present invention can be configured in a variety of ways. FIG. 4 shows end views of a variety of designs of prosthetic devices 60 having keels 62 of various shapes and angles. The keels 62 can have a thickness equal to the implant thickness or the device may have an articular body that has a different thickness than the keels or be non-uniformly thick.

Figure 5:
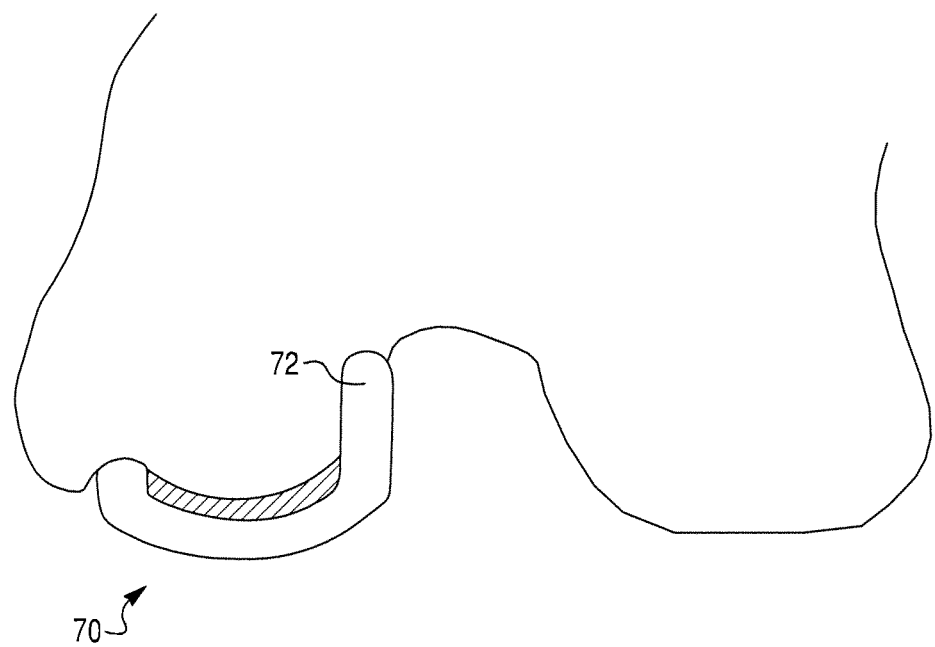
FIG. 5 is a cross-sectional view of a prosthetic device with a keel that is offset to a perimeter or edge of the prosthetic device, according to an example.

In the embodiments shown in FIGS. 1 through 4, keels are provided on both sides of the centerline of the body portion. However, a single offset keel can be provided that is only on one side of the centerline. FIG. 5 shows an example of a prosthetic device 70 with a keel 72 that is offset to a perimeter or edge of the prosthetic device 70.

Figure 6:
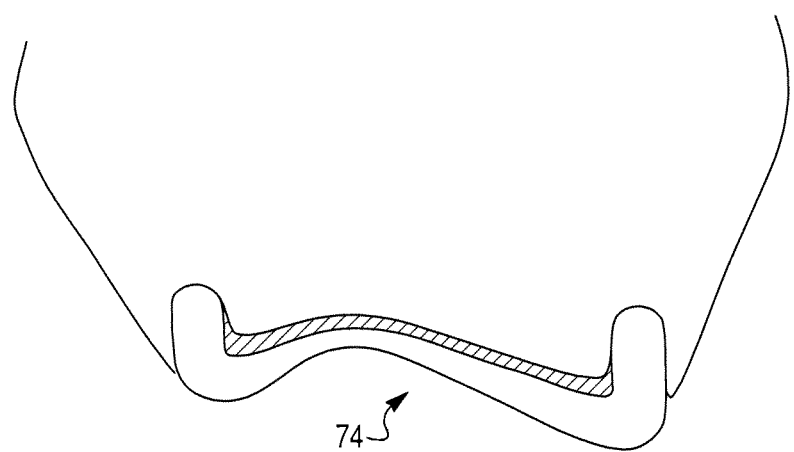
FIG. 6 is a cross-sectional view of a patellofemoral component, according to an example.
Figure 7:
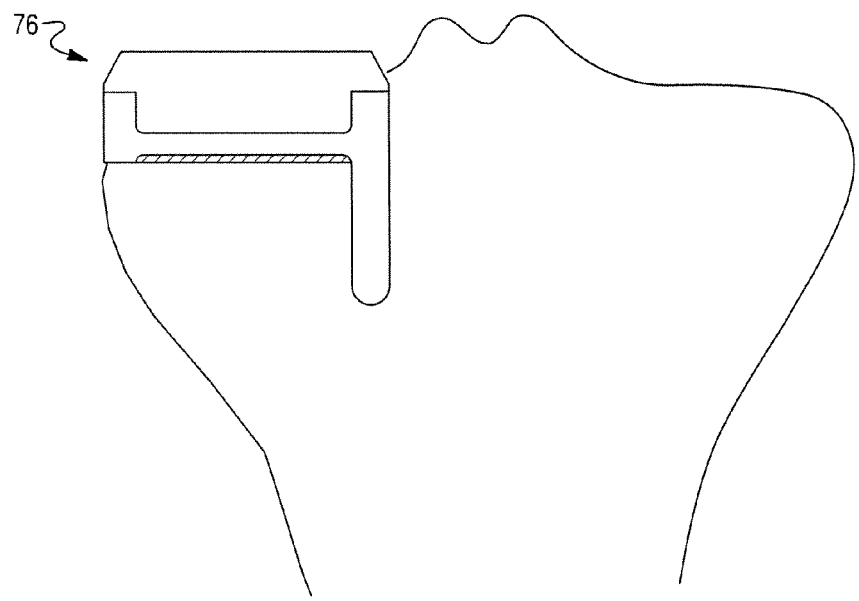
FIG. 7 is a cross-sectional view of a tibial baseplate, according to an example.
Figure 8A:
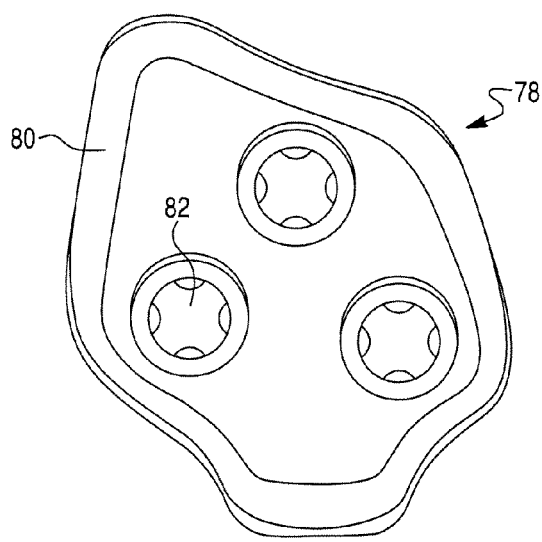
FIG. 8a is an end view of an implant, according to an example.
Figure 8B:
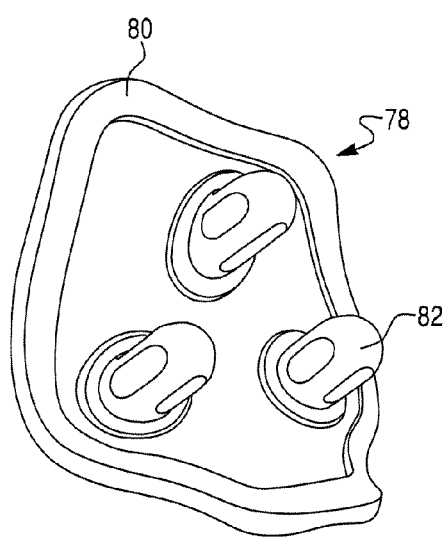

In the embodiments shown in FIGS. 1 through 4, keels are provided on femoral components. However, the invention can be applied to other prosthetic devices, such as, for example, a patellofemoral component (e.g., the component 74 shown in the example of FIG. 6) or a tibial baseplate (e.g., the component 76 shown in the example of FIG. 7) or tibial inlay. A further example of a patellofemoral prosthetic device 78 is shown in the end and perspective views of FIGS. 8a and 8b, respectively, having a keel 80 provided on perimeter or edge of the prosthetic device 78 and one or more pegs 82 to enhance the attachment of the prosthetic device 84 to bone.

Figure 9A:
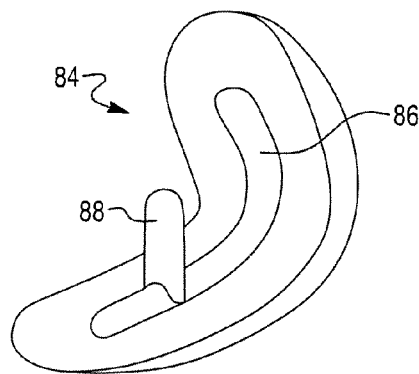
FIG. 9a is a perspective view of an implant with an internal keel, according to an example.
Figure 9B:
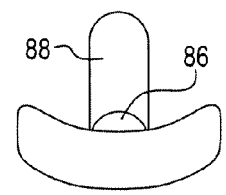
Figure 9C:
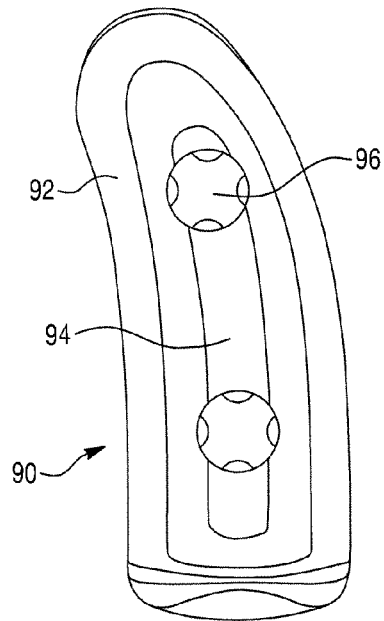
FIG. 9c is an end view of an implant with an internal keel, according to an example.
Figure 9D:
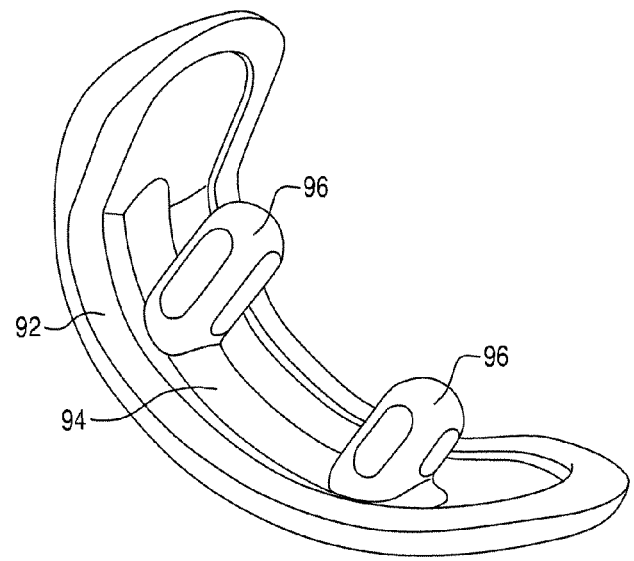
FIG. 9d is a perspective view of the implant of FIG. 9c.
Figure 10:
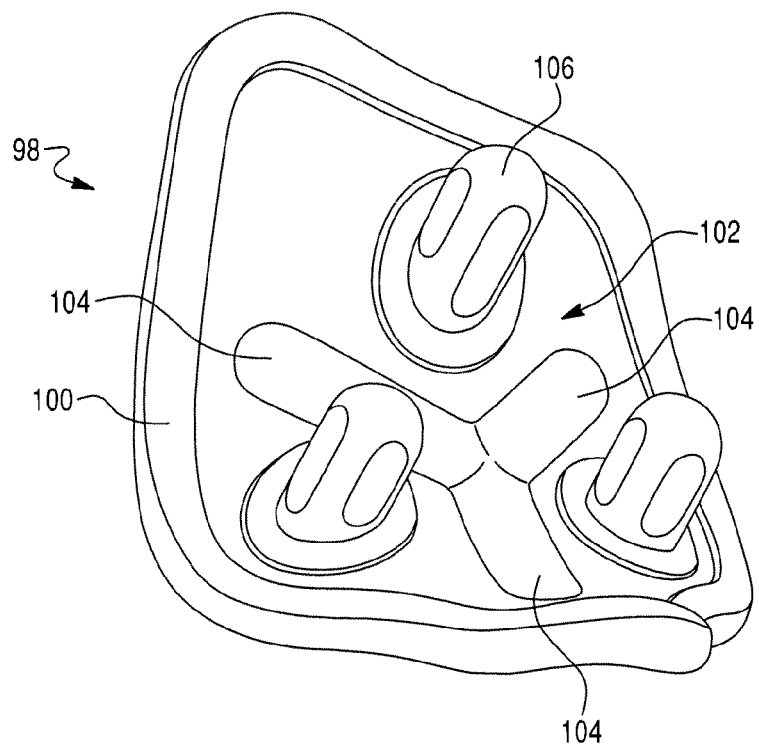
FIG. 10 is a perspective view of an implant with an internal keel, according to an example.

A prosthetic device 84 also can include an internal keel 86, 94, 104, as shown in the examples of FIGS. 9a through 9d and 10. In particular, FIGS. 9a and 9b show perspective and end cross-sectional views, respectively, of a prosthetic device 84 having an internal keel 86 and one or more pegs 88 along the centerline. FIGS. 9c and 9d show a prosthetic device 90 that includes an internal keel 94 and one or more pegs 96 along the centerline, in addition to the keels 92 provided at a perimeter or edge of the prosthetic device 90. FIG. 10 shows a prosthetic device 98 in the form a patellofemoral component that includes an internal keel 102 in addition to the keels 100 provided at an edge or perimeter of the prosthetic device 98. The internal keel 102 can branch into one or more arms 104 so that different internal regions of the prosthetic device 98 can be strengthened where the arms 104 are present.

A prosthetic device according to the present invention also may have an asymmetric structure. For example, the keel or keels of a prosthetic device can be designed such that the keels are asymmetrical in regard to a longitudinal centerline of a prosthetic device. In such asymmetrical designs, the keel or keels are preferably placed on a lateral side of a medial prosthetic device. This facilitates revision with a saw or osteotome because the laterally positioned keel advantageously provides substantial access to a majority of the bone fixation surface.

Figure 11:
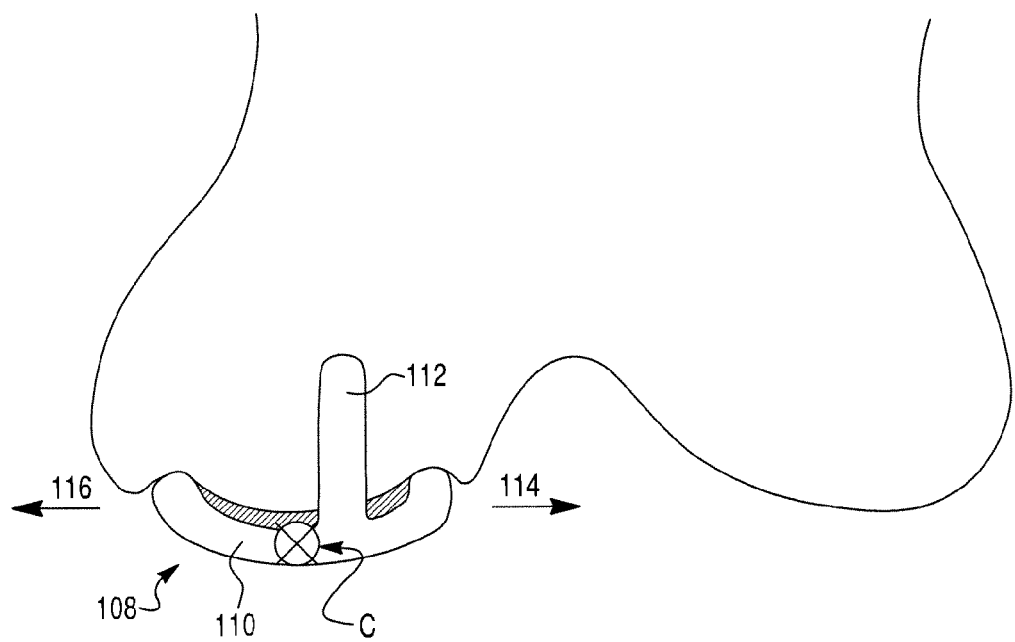
FIG. 11 is a cross-sectional view of an implant with an asymmetrical keel structure offset from a center of the implant, according to an example.

FIG. 11 shows an example of such a prosthetic device 108 with an asymmetric structure. The prosthetic device 104 includes a body portion 110 and a keel 112. The keel 112 can be located on the body portion 110 such that the keel 112 is offset from the longitudinal centerline C of the prosthetic device 108. Preferably it is offset towards the lateral direction 114 of a medial prosthetic device rather than the medial direction 116 as the arthrotomy and implant access is most often made from the medial side. In such a configuration, it may be necessary for the keel 112 to be as large as conventional central keels to achieve the desired connection, strength, and stiffness. Nevertheless, the offset keel 112 provides advantages in revision that will be described below.

Figure 12A:
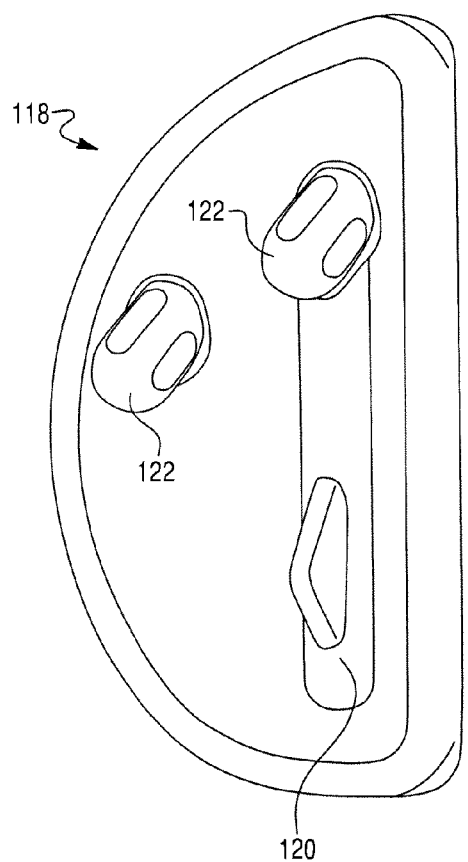
FIG. 12a is a perspective view of an implant with an asymmetrical keel structure, according to an example.
Figure 12B:
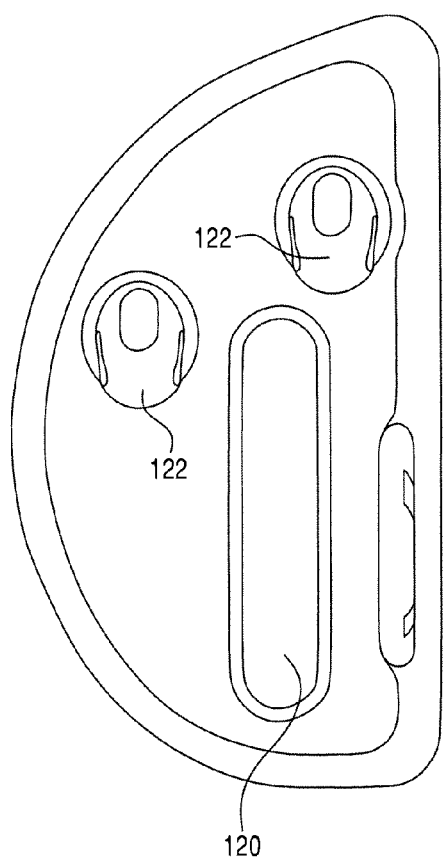

FIGS. 12*a* and 12*b* show another example of a prosthetic device 118 that includes an asymmetrical design with an offset keel 120. The prosthetic device 118 can include one or more pegs 122. The prosthetic device 118 of FIGS. 12*a* and 12*b* can be used, for example, as a tibial baseplate in a knee joint.

Figure 13:
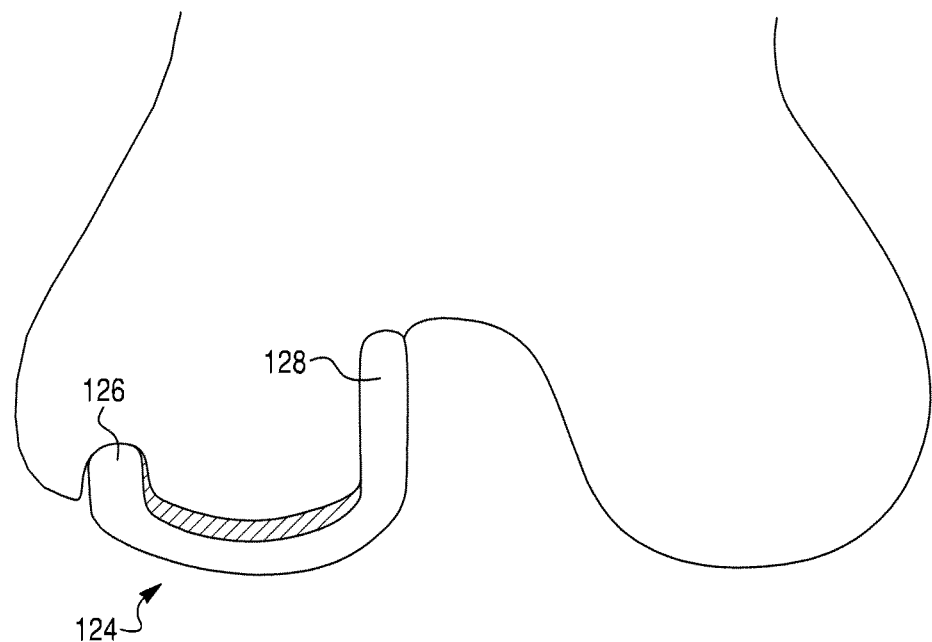
FIG. 13 is a cross-sectional view of a prosthetic device with keels having different heights, according to an example.

A prosthetic device also can have multiple keels that are asymmetric relative to one another. FIG. 13 shows an example of a prosthetic device 124 with two keels 126, 128 having different heights, with keel 128 being taller than keel 126. The keels 126, 128 also could be asymmetric by having different widths.

Figure 14:
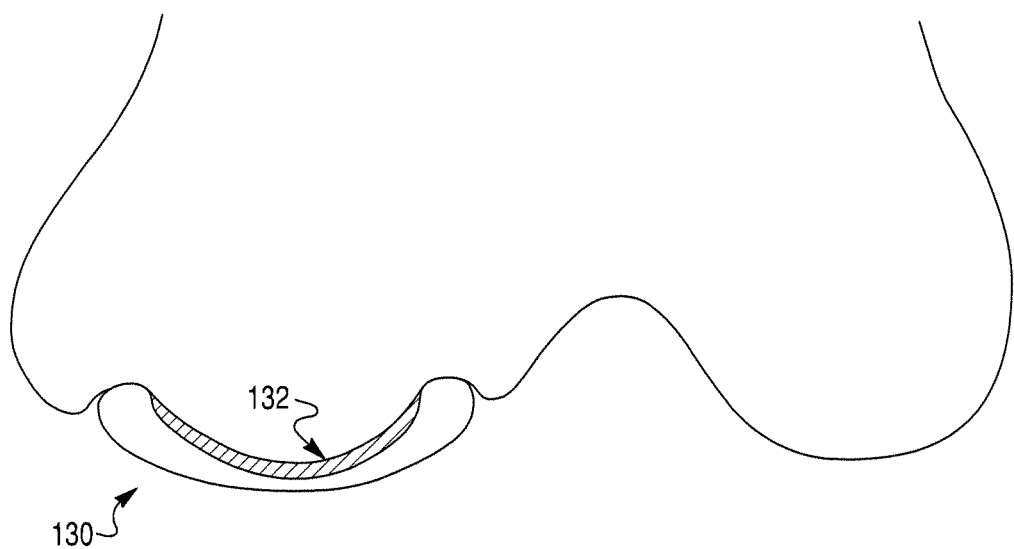
FIG. 14 is a cross-sectional view of a prosthetic device with an articular section having a non-uniform thickness, according to an example.

The articular section of the prosthetic device can have a non-uniform thickness. FIG. 14 shows an example of a prosthetic device 130 having an articular section 132 that can act as a bearing surface to replace at least a portion of a bone of a knee joint and can be shaped to contact and slide across an opposing implant or bone in the knee joint. As can be seen in FIG. 14, the articular section 132 does not have a uniform thickness.

Figure 15:
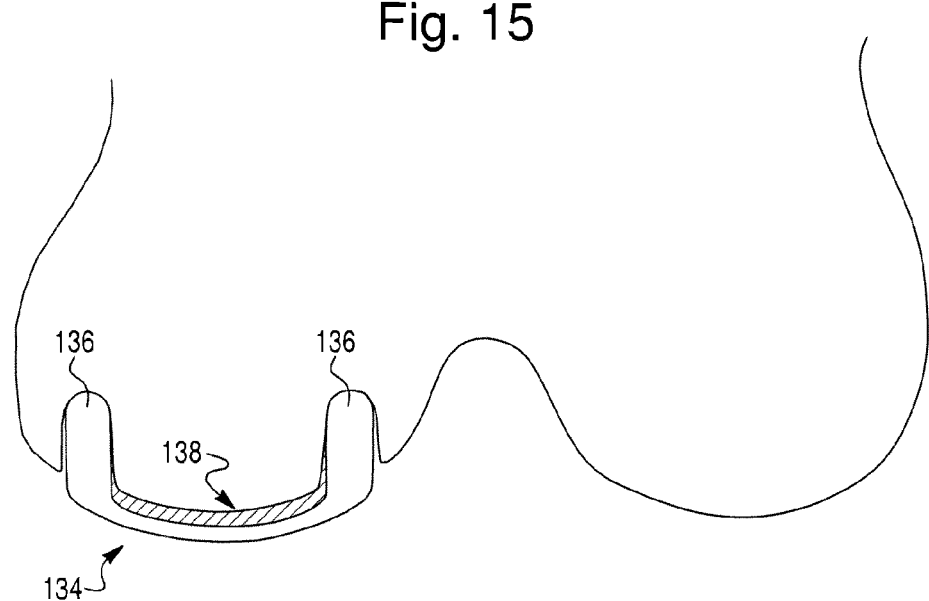
FIG. 15 is a cross-sectional view of a prosthetic device with an articular section having a thickness that is different than a keel width, according to an example.

The articular section of the prosthetic device also may have a thickness that is different from the width of each keel and the overall thickness provided by the keel(s). As shown in the example of FIG. 15, the prosthetic device 134 has an articular section 132 and keels 136 at a perimeter or edge of the prosthetic device 134. The articular section 132 has a thickness different from the width of the keels 136 and, in the center portion, is less than the overall thickness at the location of the keels 136.

Implantation of Prosthetic Devices

Figure 16A:
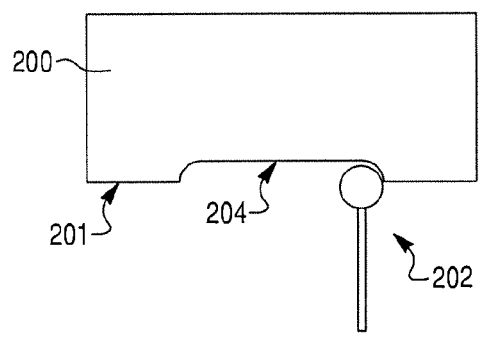
FIG. 16a is a cross-sectional view showing a step of forming a body portion void in a bone, according to an example.
Figure 16B:
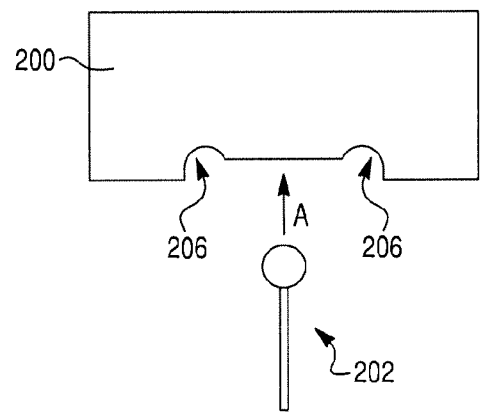
Figure 16C:
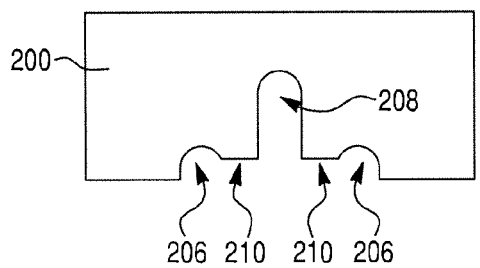
FIG. 16c is a cross-sectional view showing the bone of FIG. 16b with a void for a peg.
Figure 16D:
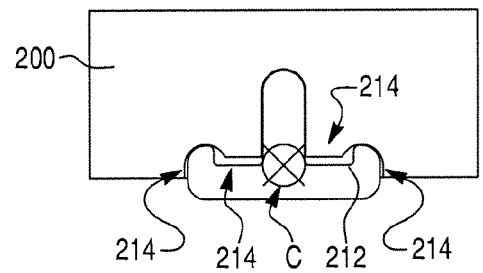
FIG. 16d is a cross-sectional view of the bone of FIG. 16c with an implanted prosthetic device.

Prosthetic devices according to the present invention can be implanted on a bone in a joint using a relatively simple procedure with fewer tools in shorter time than conventional implant designs. FIGS. 16*a* through 16*d* show one such process for implanting a prosthetic device. In FIG. 16*a*, a first portion of bone 200 is removed by a tool 202 to provide a void 204 configured to receive a body portion of a prosthetic device and extending into the bone 200 a body portion depth from an original surface 201 of the bone 200. In FIG. 16*b*, the same tool 202 can be used to remove at least one second portion from the bone 200 to form at least one keel void 206 to receive a keel projecting from the body portion, with the keel void 206 extending into the bone 202 at a keel depth from the original surface 201 of the bone that is greater than the body portion depth. The keel void 206 is configured to receive a keel of a prosthetic device that extends along a longitudinal direction of the body portion and is offset from a longitudinal center of a prosthetic device. The same tool 202 can be advanced in the direction indicated by arrow A (FIG. 16*b*) to form a peg void 208 (FIG. 16*c*), if the prosthetic device includes one or more pegs. After the body portion void 204, the keel void(s) 206, and the peg void(s) 208 have been cut into the bone 200, a prosthetic device 212 can be inserted into the voids 204, 206, 208, as shown in FIG. 16*d*. Cement 214 may be provided between the body portion of the prosthetic device 212 and the bone to help secure the prosthetic device 212 in position.

As shown in the example of FIGS. 16*a* through 16*d*, the same, single tool can be used to cut the voids in the bone for the prosthetic device. For example, a single tool having a shape corresponding the shape of a prosthetic device, particularly the shape of the keel or keels of the prosthetic device, can be used to resect portions of bone to provide voids or openings that the prosthetic device and the keels of the prosthetic device correspond to. A spherical sculpting burr, for example, can be used to cut circular voids corresponding to keels with rounded surfaces. The use of a single tool to prepare the bone reduces the amount of time needed in an operating room because the tool does not have to be exchanged for another. Conventional prosthetic devices with tall, narrow keels often require multiple tools in addition to a first tool, such as a small diameter burr, such as a router burr, or a sagittal saw. This switching between tools increases operating room time and cost, which can be minimized with the processes described herein.

The keels of the prosthetic device preferably have cross-sectional shapes along the medial-lateral direction M-L that match the shapes of the voids formed by the tool 202. For example, the keels can have a convex, arcuate shape that matches with a concave, arcuate cross-sectional shape formed by the tool 202 in the bone. Thus, the keels can be configured to position the prosthetic device during implantation. The keels also can promote attachment of the prosthetic device to bone in a knee joint by interlocking with the voids provided in the bone.

Figure 17A:
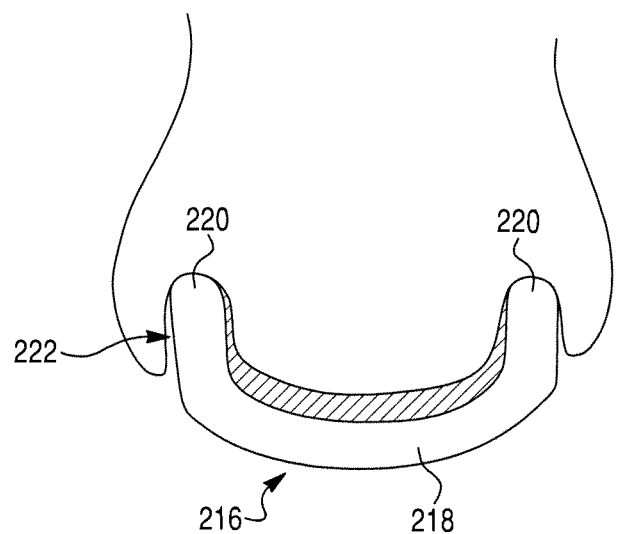
FIG. 17a is a cross-sectional view of a prosthetic device with keels, according to an example.
Figure 17B:
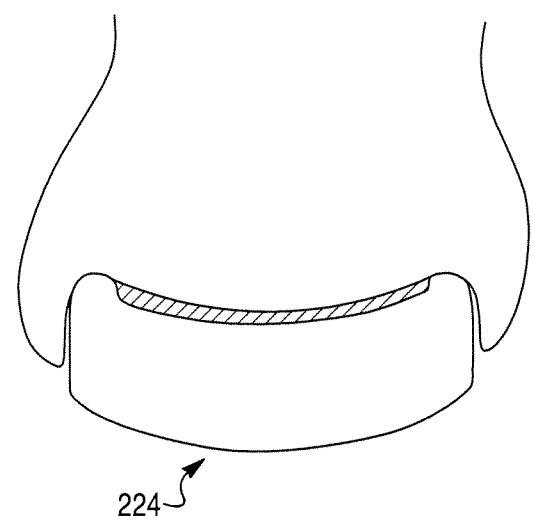
FIG. 17b is a cross-sectional view of a prosthetic device having an overall thickness the same as the prosthetic device of FIG. 17a but require less bone resection, according to an example.

The use of two keels, preferably at the perimeter of the prosthetic device, can reduce the amount of bone resection because less of the prosthetic device penetrates into the bone. FIG. 17*a* shows an example of a prosthetic device 216 with keels 220 offset from a longitudinal centerline of a body portion 218 of the prosthetic device 216. The keels 220 permit the prosthetic device 216 to have an overall thickness that is equivalent to the prosthetic device 224 shown in FIG. 17*b*, while requiring less bone resection. Greater bone resection is required for the prosthetic device 224 of FIG. 17*b* due to its relatively large thickness throughout the articular section.

Figure 18:
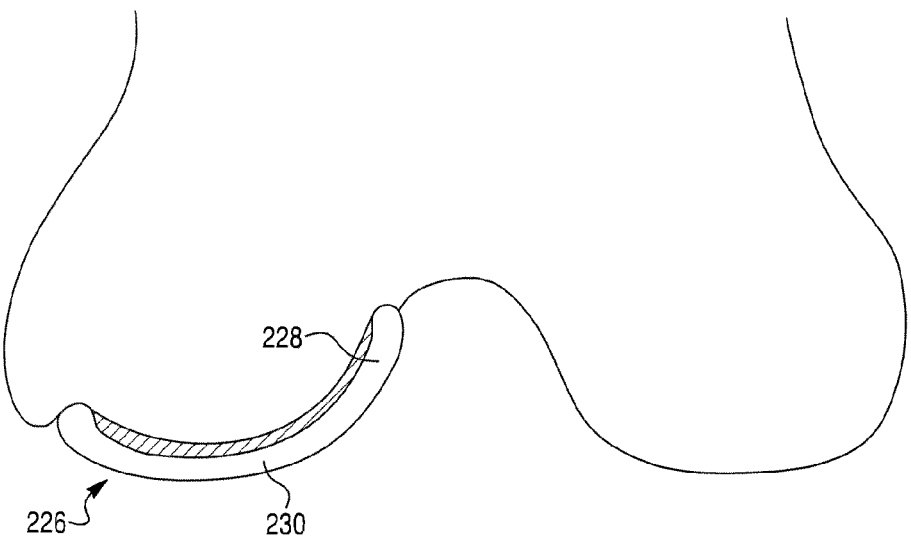
FIG. 18 is a cross-sectional view of a prosthetic device with a keel that is angled relative to a bone, according to an example.
Figure 19A:
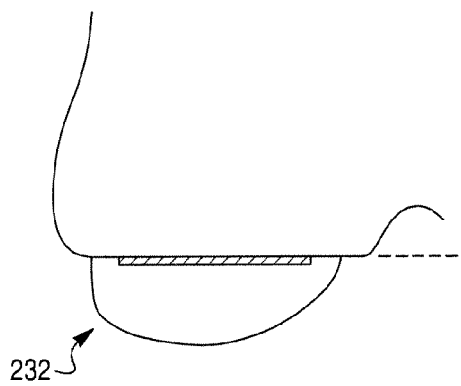
FIG. 19a is a cross-sectional view of a prosthetic device, according to an example.
Figure 19B:
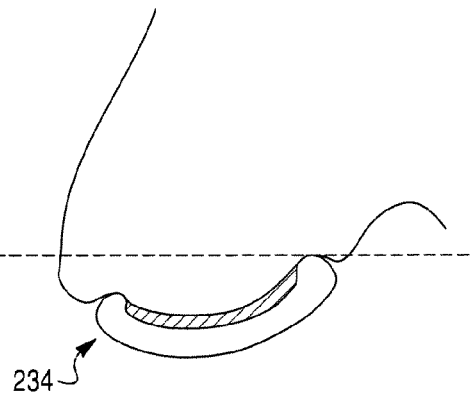
FIG. 19b is a cross-sectional view of a prosthetic device with a keel angled relative to a bone to reduce an amount of bone resection relative to the prosthetic device of FIG. 19a, according to an example.

A keel or keels of a prosthetic device can be angled with respect to a bone to reduce the necessary amount of bone resection. FIG. 18 shows an example of a prosthetic device 226 with a body portion 230 and a keel 228 that is angled with respect to a bone. The angled keel has an angle that is preferably less than or equal to 45° with respect to the longitudinal centerline. Such an angle, for example, can be selected to reflect an angle of curvature of a bone to which the prosthetic device is attached. FIGS. 19*a* and 19*b* illustrate how the angled keel(s) reduce bone resection. To obtain an equivalent effective thickness, the non-angled prosthetic device 232 of FIG. 19*a* requires much more bone resection than the angled prosthetic device 234 of FIG. 19*b*. The dashed line between FIGS. 19*a* and 19*b* illustrates the effective thicknesses of the prosthetic devices 232, 234.

Figure 20A:
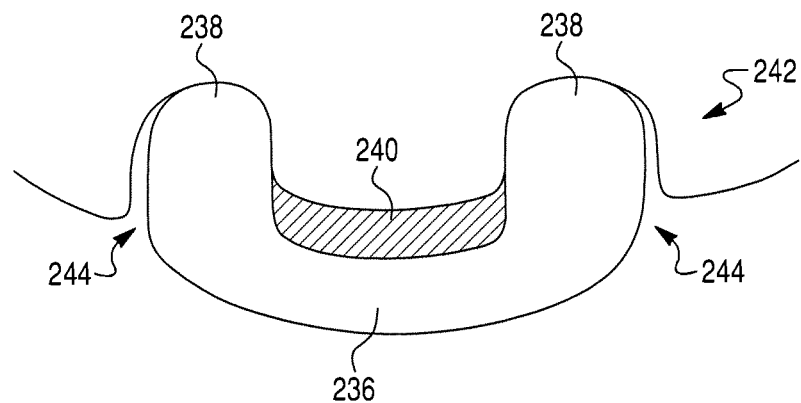
FIG. 20a is an end cross-sectional view of an implant with a cement pocket, according to an example.
Figure 20B:
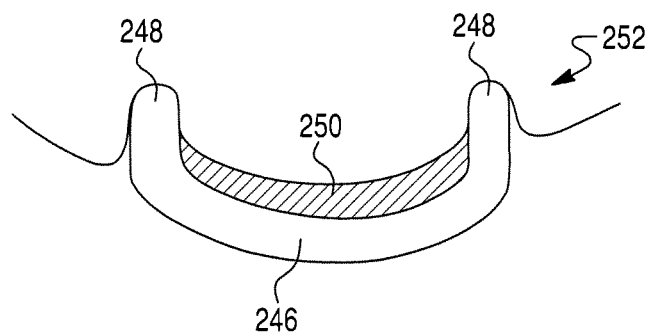
FIG. 20b is an end cross-sectional view of an implant with a cement pocket, according to an example.

The keels and voids can be designed to have other, corresponding shapes and geometries, as shown in FIGS. 20*a* and 20*b*. In FIG. 20*a*, a prosthetic device 236 has relatively wider keels 238 that are attached to a bone 242. Portions of the bone 242 can be resected to form voids 244 to receive the keels 238 of the prosthetic device 236, thus promoting attachment of the prosthetic device 236 to the bone 242. In addition, the keels 238 can form an area 240 between the keels 238 for cement that is contained between the prosthetic device 236 and the bone 242, which also promotes attachment of the prosthetic device 236 to the bone 242. In FIG. 20*b*, another example of a prosthetic device 246 has relatively narrower keels 248 that can be inserted into recesses or voids of a bone 252, with the keels 248 forming an area 250 for cement to be contained between the prosthetic device 246 and the bone 252.

Figure 21A:
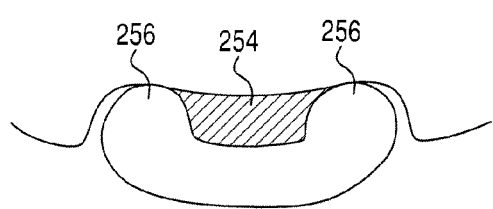
FIG. 21a is an end cross-sectional view of an implant, according to an example.
Figure 21B:
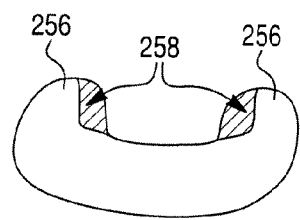
FIG. 21b is an end cross-sectional view of the implant of FIG. 21a with truncated keels.
Figure 21C:
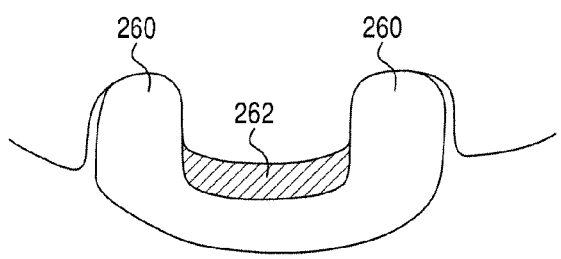
FIG. 21c is an end cross-sectional view of an implant, according to an example.
Figure 21D:
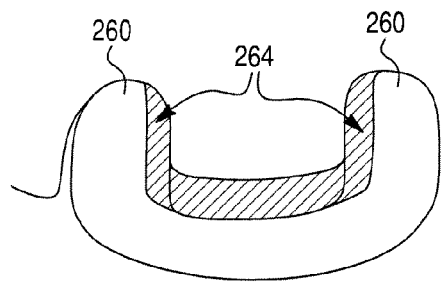
FIG. 21d is an end cross sectional view of the implant of FIG. 21c with truncated keels.

In addition, the keels and voids can be designed to have differing shapes and geometries. FIG. 21a is an end cross-sectional view of an exemplary prosthetic device with keels 256 that are disposed into a void of substantially one depth, which forms a pocket for cement 254. FIG. 21c is another end cross-sectional view of an exemplary prosthetic device with keels 260 that fit within keel voids but nevertheless form a pocket for cement 262. As shown in the example of FIGS. 21b and 21d, the keels 256, 260 can be truncated by removing sections 258, 264 of the keels 256, 260, which provides additional area for cement in the areas between the keels 246, 260, thus further promoting attachment of the prosthetic devices to bone.

The above described process can not only be used for prosthetic devices with multiple keels, but also can be used for prosthetic devices having only a single offset keel, such as the prosthetic device 108 of FIG. 11.

Revision of Prosthetic Devices

Prosthetic devices according to the present invention also can facilitate revision through the use of procedures that require less removal of bone than conventional procedures. For example, the present invention provides a method of removing from a bone a prosthetic device having a body portion and a keel offset from a longitudinal centerline of the body portion and inserted into a keel void in the bone to a keel depth.

In the case of a prosthetic device according to the present invention having multiple keels, less bone needs to be removed than in conventional techniques. The multiple keels can be configured to extend to less of depth in the bone (while maintaining the connection, strength, and stiffness). Thus, if the prosthetic device is removed by removing bone to a depth that is the same as the depth of the keels, less bone ultimately will be removed than with a conventional large central keel. With a large central keel, a saw or osteotome is used to remove as much bone as possible from the device's fixation surfaces and cement pockets. If the central keel adheres to bone through ongrowth or by cement, much of the adjacent bone can be inadvertently removed leaving a large void that needs to be filled with an augment attached to the subsequent device.

In the case of a prosthetic device according to the present invention having an asymmetric design (e.g., only a single offset keel), again less bone needs to be removed than in conventional techniques. For example, a single keel can be located on a lateral side of the longitudinal centerline of the body portion of the prosthetic device (see FIG. 10). The resecting of bone material can be initiated from a medial side of the bone (i.e., on a side opposite to the lateral portion of the bone where a keel is located). The keel can be relatively easy to remove from the keel void after the connection is broken between the bone and the majority of the body portion. Thus, the bone can be resected starting on the medial side and at a depth that is less than the keel depth. The resection continues until reaching the keel on the lateral side. Because the connection has been broken between the bone and the majority of the body portion by the resection from the medial side to the lateral side, the keel typically can be removed from the bone to complete the removal of the prosthetic device. Using this process, bone is removed to a depth less than the keel depth, which preserves more bone than conventional techniques.

Figure 22A:
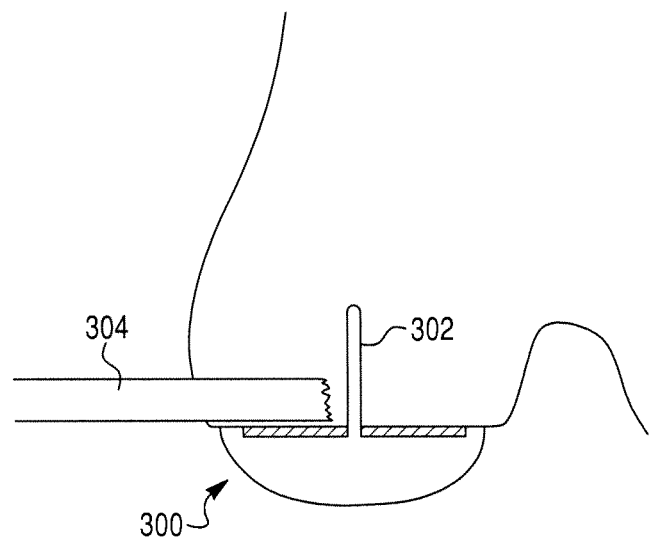
FIG. 22a is a cross-sectional view of a revision step for a conventional prosthetic device with a central keel, according to an example.
Figure 22B:
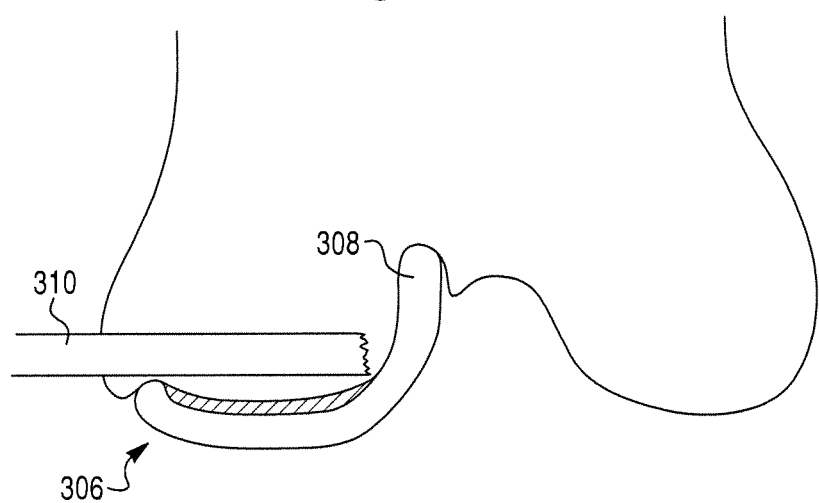
FIG. 22b is a cross-sectional view of a revision step for a prosthetic device with an offset keel, according to an example.

To illustrate this point, FIG. 22a shows an example of a revision step for a conventional prosthetic device 300 with a central keel 302 in which a tool 304 is used to cut into a bone to free and remove the device 300 from the bone. The saw cannot proceed past the keel 302, and therefore a deeper cut into the bone is required or bone on the lateral side may be lost during forced removal of the device 300. In contrast, FIG. 22b shows an example of a step to revise a prosthetic device 306 with an offset keel 308, which is relatively easy to remove from a bone during a revision process. For example, a tool 310, such as a saw or osteotome, can be used to resect at least a portion of bone from beneath the prosthetic device 306, which permits the prosthetic device 306 and keel 308 to be removed from the bone with relative ease with the tool due to the relatively less penetration that the keel 308 provides into a bone.

Other embodiments of the present invention will be apparent to those skilled in the art from consideration of the specification and practice of the invention disclosed herein. It is intended that the specification and examples be considered as exemplary only.

What is claimed is:

1. A prosthetic implantation system, comprising:
 a cutting tool comprising a spherical burr adapted for preparing a surface of a bone of a joint, the prepared surface including a body portion void and a keel void, the keel void extending into the bone at a depth greater than the body portion void; and
 a prosthetic component comprising:
 a body portion for attachment to the bone of the knee joint and having a bearing surface configured to replace at least a portion of the bone and an implantation surface configured to engage the body portion void; and
 a keel configured to be inserted into a corresponding keel void formed in the bone, wherein the keel projects outwardly from the implantation surface by an amount sufficient to inhibit movement of the body portion relative to the bone in both medial and lateral directions upon insertion into the keel void,
 wherein the keel extends along a longitudinal direction of the body portion and has a substantially uniform height above the implantation surface, wherein the substantial uniformity of the height remains continuous along a majority of the extent of the keel in the longitudinal direction, and
 wherein a cross-sectional shape of the spherical burr used to form the keel void matches a rounded cross-sectional surface of the keel.

2. The prosthetic implantation system of claim 1, wherein the implantation surface is substantially curved along a longitudinal direction of the body portion.

3. The prosthetic implantation system of claim 1, wherein the cross-sectional surface of the keel has a convex, arcuate, cross-sectional shape along a medial-lateral direction.

* * * * *